United States Patent
Tyrrell et al.

(10) Patent No.: US 7,037,535 B2
(45) Date of Patent: May 2, 2006

(54) METHOD AND COMPOSITION FOR NEUTRALIZING HOUSE DUST MITE FECES

(75) Inventors: David J. Tyrrell, Appleton, WI (US); Duane G. Krzysik, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 59 days.

(21) Appl. No.: 10/299,868

(22) Filed: Nov. 19, 2002

(65) Prior Publication Data

US 2004/0096525 A1 May 20, 2004

(51) Int. Cl.
*A61K 35/78* (2006.01)
*A01N 25/00* (2006.01)

(52) U.S. Cl. .............. 424/766; 424/735; 424/730; 424/732; 424/736; 424/765; 424/737; 424/405

(58) Field of Classification Search .............. 424/725, 424/729, 730, 732, 736, 765, 737, 405
See application file for complete search history.

(56) References Cited

U.S. PATENT DOCUMENTS

| | | | |
|---|---|---|---|
| 4,100,324 A | 7/1978 | Anderson et al. | |
| 4,255,337 A | 3/1981 | Kaiser et al. | |
| 4,609,547 A | 9/1986 | Garman et al. | |
| 4,806,526 A * | 2/1989 | Green | 514/23 |
| 5,141,803 A | 8/1992 | Pregozen | |
| 5,152,996 A | 10/1992 | Corey et al. | |
| 5,472,700 A | 12/1995 | Staetz et al. | |
| 5,512,283 A | 4/1996 | Byers et al. | |
| 5,587,358 A | 12/1996 | Sukigara et al. | |
| 5,601,833 A | 2/1997 | Ribier et al. | |
| 5,604,262 A | 2/1997 | Wood | |
| 5,648,083 A | 7/1997 | Blieszner et al. | |
| 5,656,278 A | 8/1997 | Enjolras | |
| 5,723,138 A | 3/1998 | Bae et al. | |
| 5,804,168 A | 9/1998 | Murad | |
| 5,830,916 A | 11/1998 | Hannun et al. | |
| 5,851,782 A | 12/1998 | Hannun et al. | |
| 5,888,524 A | 3/1999 | Cole | |
| 5,906,992 A | 5/1999 | Fonsny et al. | |
| 5,916,573 A | 6/1999 | Spiers et al. | |
| 5,916,917 A * | 6/1999 | Suh et al. | 514/544 |
| 5,935,596 A | 8/1999 | Crotty et al. | |
| 5,985,300 A | 11/1999 | Crotty et al. | |
| 6,028,018 A | 2/2000 | Amundson et al. | |
| 6,060,075 A | 5/2000 | Rao et al. | |
| 6,117,440 A * | 9/2000 | Suh et al. | 424/407 |
| 6,174,519 B1 | 1/2001 | Greene | |
| 6,235,272 B1 | 5/2001 | Greene | |
| 6,235,737 B1 | 5/2001 | Styczynski et al. | |
| 6,258,355 B1 | 7/2001 | Cavaliere widow Vesely et al. | |
| 6,800,247 B1 * | 10/2004 | Suh et al. | 422/28 |
| 2001/0048097 A1 * | 12/2001 | Inui et al. | 252/365 |
| 2002/0022043 A1 | 2/2002 | Miller | |

FOREIGN PATENT DOCUMENTS

| | | |
|---|---|---|
| AU | 199857398 B2 | 4/1997 |
| CN | 1071844 A | 5/1993 |
| CN | 1280008 A | 1/2001 |
| DE | 19824680 A1 | 12/1999 |
| DE | 19824683 A1 | 12/1999 |
| DE | 19824727 A1 | 12/1999 |
| DE | 19827624 A1 | 12/1999 |
| DE | 10104479 C1 | 9/2002 |
| EP | 350275 B1 | 2/1994 |
| EP | 870507 A1 | 3/1998 |
| EP | 993822 A1 | 9/1999 |
| GB | 2363074 A | 12/2001 |
| JP | 59-166585 A | 3/1983 |
| JP | 01-207339 A | 2/1988 |
| JP | 03-029623 A | 6/1989 |
| JP | 03-236311 A | 2/1990 |
| JP | 07-228892 A | 2/1994 |
| JP | 06279273 * | 10/1994 |
| JP | 08-217658 A | 2/1995 |
| JP | 08-268859 A | 4/1995 |
| JP | 08-294395 A | 5/1995 |
| JP | 09-110615 A | 10/1995 |
| JP | 09-194317 A | 1/1996 |
| JP | 11-116417 A | 10/1997 |
| JP | 11-130627 A | 10/1997 |
| JP | 11-139959 A | 11/1997 |

(Continued)

OTHER PUBLICATIONS

Ando et al. Clinical Experimental Allergy: Journal of the British Society for Allergy and Clinical Immunology. 1993. vol. 23, No. 9, pp. 777-784, MEDLINE Abstract enclosed.*
Abe et al. Biochemical and Biophysical Research Communication. 2000. vol. 268, pp. 767-771.*
Calderone, R.A. et al., Adherence and Receptor Relationships of *Candida albicans*, Microbiological Reviews, (1991), pp. 1-20, vol. 55:1.
Hostettler, M.K., Adhesions and Ligands Involved in the Interaction of *Candida* spp. With Epithelial and Endothelial Surfaces, Clinical Microbiology Reviews, (1994), pp. 29-42, vol. 7:1.

(Continued)

*Primary Examiner*—Christopher R. Tate
(74) *Attorney, Agent, or Firm*—Senniger Powers

(57) ABSTRACT

Methods for neutralizing dust mite feces are disclosed. In one embodiment, a botanical extract having a BAPNA-Trypsin Inhibition ($IC_{50} \times 10^{-3}$ (%, v/v or w/v) of from about 0.01 to about 500 and a sufficient solubility in water is introduced into water to form an aqueous botanical extract solution. The aqueous botanical extract solution is atomized into an area being treated such that the botanical extract contacts and neutralizes the dust mite feces located in the area. Particularly preferred botanical extracts for use in the botanical extract aqueous solutions of the present invention include Green Tea Extra and Grape Seed Extract.

24 Claims, No Drawings

FOREIGN PATENT DOCUMENTS

| | | |
|---|---|---|
| JP | 11-228325 A | 2/1998 |
| JP | 11-292710 A | 4/1998 |
| JP | 11-332778 A | 5/1998 |
| JP | 2000-053923 A | 8/1998 |
| JP | 2000-063262 A | 8/1998 |
| JP | 2000-153533 A | 8/1998 |
| JP | 2000-0700097 A | 8/1998 |
| JP | 2000-169359 A | 4/1999 |
| JP | 2001-009950 A | 6/1999 |
| JP | 2001-261543 A | 3/2000 |
| KR | 9708991 B1 | 5/1997 |
| WO | WO 96/09762 A1 | 4/1996 |
| WO | WO 98/03147 A1 | 1/1998 |
| WO | WO 96/22015 A1 | 7/1998 |
| WO | WO 98/36640 A1 | 8/1998 |
| WO | WO 98/42303 A1 | 10/1998 |
| WO | WO 98/44901 A1 | 10/1998 |
| WO | WO 98/44926 A1 | 10/1998 |
| WO | WO 99/07220 A1 | 2/1999 |
| WO | WO 99/15208 A2 | 4/1999 |
| WO | WO 99/53763 A1 | 10/1999 |
| WO | WO 99/62478 A1 | 12/1999 |
| WO | WO 99/66897 A1 | 12/1999 |
| WO | WO 9966796 A1 | 12/1999 |
| WO | WO 00/32162 A1 | 6/2000 |
| WO | WO 00/44344 A2 | 8/2000 |
| WO | WO 01/00033 A1 | 1/2001 |
| WO | WO 01/00253 A1 | 1/2001 |
| WO | WO 01/01949 A1 | 1/2001 |
| WO | WO 01/19325 A1 | 3/2001 |
| WO | WO 01/26617 A1 | 4/2001 |
| WO | WO 01/76371 A1 | 10/2001 |
| WO | WO 01/83666 A2 | 11/2001 |
| WO | WO 02/28187 A1 | 4/2002 |
| WO | WO 02/062354 A1 | 8/2002 |

OTHER PUBLICATIONS

Tronchin, G. et al., Fungal Cell Adhesion Molecules in *Candida albicans*, European Journal of Epidemiology, (1991), pp. 23-33, vol. 7:1.

Billson et al., The Design and Synthesis of Inhibitors of the Cysteinyl Protease, Bioorganic & Medicinal Chem. Letters (1998), pp. 993-998, vol. 8.

International Search Report of PCT/US 03/16435 dated Sep. 30, 2003.

Di Marzio et al., Effect of the Lactic Acid Bacterial *Streptococcus thermophillus* on Ceramide Levels in Human Keratinocytes in Vitro and Stratuum Corneum In Vivo, Soc.Invest.Derm., 1999, 113(1):98-106.

Higaki et al., Staphylococcus species on the Skin Surface of Infant Atopic Dermatitis Patients, J.Inter.Med.Res., 1998, 26:98-101.

Jin et al., Analysis of beta-glucocerebrosidase and Ceramidase Activities in Atopic and Aged Dry Skin, Acta. Derm.Venerol., 1994, 74:337-340.

Marekov et al., Cermides are Bound to Structural Proteins of the Human Foreskin Epidermal Cornified Cell Envelope, J.Biol.Chem., 1998, 273(28):17763-17770.

Okino et al., Purification and Characterization of a Novel Ceramidase from *Pseudomonas aeruginosa*, J.Biol.Chem., 1998, 273(23):14368-14373.

* cited by examiner

METHOD AND COMPOSITION FOR NEUTRALIZING HOUSE DUST MITE FECES

BACKGROUND OF INVENTION

The present invention relates to a method of neutralizing allergens produced by house dust mites. More particularly, the present invention relates to a method and composition for neutralizing house dust mite feces allergens by atomizing an aqueous solution comprising a botanical extract having protease inhibitory activity such that the atomized botanical extract contacts the house dust mite feces and renders it substantially non-allergenic.

It has been known for many years that common house dust is an important cause of asthma, rhinitis and eczema in allergic individuals. Common house dust mites (*Dermatophagoides farinae* and *Dermatophagoides pteronyssinus*) are prevalent in house dust. Dust mites are not insects, but are eight-legged arachnids, and are related to ticks and spiders. Adult mites are approximately 250–300 micrometers in length, and are photophobic.

House dust mites are co-inhabitants of almost every house and, because of their size and translucent body structure, cannot be seen with the naked eye. Dust mites are found in almost all home furnishing textiles and thrive in mattresses, pillows, cushions, carpets, upholstery, and soft toys etc. An adult mite can live up to about three months. The reactions caused by house dust mite feces in sensitive people can range from itchy and watery eyes, repeated sneezing and running nose, cough and bronchial asthma, to eczema. The dust on which house dust mites thrive may be cotton, wool lint, animal and human dander or hair, crumbs, pollens, and molds.

House dust mites typically feed on human skin scales. In addition to a food source, the other essential requirement for dust mite growth is adequate humidity. Dust mites are 75% water by weight and although they do not drink water, they must absorb water vapor from the air to survive. Specialized glands above their pairs of legs produce secretions high in sodium and potassium chloride, which act to absorb water vapor from surrounding air. This can only be accomplished if the surrounding humidity is sufficiently high. Relative humidities of about 65–80% at temperatures ranging from about 20 to 35° C. are optimal for dust mite growth.

A major dust mite allergen is present in dust mite fecal particles. Each dust mite produces about 20 fecal particles per day, and more than 100,000 mites may be present in a gram of dust. These fecal particles vary from about 10 to about 40 microns in size, comparable to the size of pollen grains, and become airborne during domestic activity such as making beds and vacuuming carpets. Enzymes with serine protease and/or cysteine protease activities from house dust mite feces have been shown to damage the airway epithelium. This damage increases the propensity for house dust mite allergens (including proteases) to penetrate the protective epithelium lining, interact with immune cells, and can induce the production of specific IgE molecules which can initiate an inflammatory cascade culminating in an allergic response.

Group I allergens (*Dermatophagoides farinae* I, and *Dermatophagoides pternoyssinus* I) are heat labile, 24,000 molecular weight glycoproteins, and appear to be structural homologues and have very similar N-terminal amino acid sequences. Group I allergens are regarded as the most important and are excreted in their highest concentrations by the mite's gastrointestinal tract in the form of mite's fecal particles.

Group II allergens (*Dermatophagoides farinae* II, and *Dermatophagoides pternoyssinus* II) are 15,000 molecular weight proteins with almost identical N-terminal amino acid sequences that are also secreted by the mite's gastrointestinal tract in the form of fecal allergens, although not in as high a concentration as the group I allergens. Most dust mite allergic individuals produce antibodies to both the group I and group II allergens.

The control of dust mite population in the domestic environment is one method of preventing house dust allergies. The degree of cleanliness impacts the number of house dust mites and the resulting allergen level. Common control measures include vacuum cleaning, frequent washing, and treating the carpets and bed spreads with insecticides, acaricides, and fungicides. Reducing dust mite population by interfering with the food chain has also been suggested.

Rao et al. in U.S. Pat. No. 6,060,075 disclose a composition for controlling house dust mite population. The composition comprises a plant derived acaricidal agent, which is disclosed as neem seed kernel extract, and a plant derived disinfectant agent, which is disclosed as an alcoholic extract of resins like stryax benzoin. Rao et al. disclose that a bi-weekly spray of 200 microliters/100 milligrams of culture is required for eight weeks to completely eliminate the house dust mites, and discloses that re-establishment of house dust mites after treatment with acaricides is a common problem due to the existence of nymph and eggs. Rao et al., however, fail to disclose any compositions or methods for neutralizing the feces allergen of dust mites, and simply disclose a very narrow composition for killing house dust mites, which does not necessarily neutralize the feces.

Miller in published U.S. Patent Application 2002/0022043 discloses a method for killing house dust mites in clothing and other soft materials. Miller exposes woolen or other fabrics to the vapors of certain plant oils, including wintergreen oil, lavandin oil, Ylang-Ylang oil and others. The oils are aromatherapy-grade oils produced by steam distillation. Miller generates vapors of the oils numerous ways including: placing a few drops of the oil on a paper towel, piece of cotton, or on a glass or plastic dish and then placing the treated substrate in a closed environment with the articles to be treated; spraying a mist of the oil onto the substrate to be treated, or by heating the oil to cause vaporization. Similar to Rao, Miller sets forth a method for killing house dust mites, but does not disclose methods or compositions for neutralizing house dust mite feces. Additionally, the compositions set forth by Miller are oils which can be messy to work with, can stain certain fabrics, and can be very difficult to effectively vaporize.

McKechnie et al. in UK Patent Application GB 2,363,074 disclose a method for deactivating house dust mite allergens by volatilizing an oil which comprises tea tree oil or another oil comprising terpene compounds and contacting the volatilized oil with the house dust mite feces. McKechnie et al. volatilize the oil in numerous ways including: heating the oil to form vapors; vaporizing the oil from a heated wick dipped into a reservoir of the oil; and by utilizing an ultra-sonic jet nebuliser which contains water with the oil floated on the surface of the water. As with Miller discussed above, tea tree and other oils which are not water soluble can be difficult to work with and difficult to effectively vaporize.

Based on the foregoing, a simple, cost effective method of neutralizing the feces allergens of house dust mites is needed. The method preferably will involve simple, water soluble, compositions which are easy to work with and easily atomizable, in contrast to the oils disclosed in the prior art.

SUMMARY OF THE INVENTION

The present invention relates to neutralizing allergenic dust mite feces by contacting the dust mite feces with botanical extracts having protease inhibitory activity to reduce the allergenicity of the dust mite feces. Substantially water soluble botanical extracts, such as Green Tea Extra or Grape Seed Extract, for example, are introduced into water to form an aqueous botanical extract solution. The botanical extract, which may be in powder form or in aqueous form, used to form the aqueous botanical extract solution has a BAPNA-Trypsin inhibition ($IC_{50}\times10^{-3}$ (%, v/v or w/v)) of from about 0.01 to about 500, and preferably has a solubility in water of at least about 0.5% by weight if the botanical extract is a solid or at least about 10% by weight if the botanical extract is a liquid. Because the botanical extracts suitable for use in the present invention have a high solubility in water, they are easily and conveniently aerosolized such that large areas can easily be treated. In one embodiment of the present invention, the aqueous botanical extract solution is introduced into an atomizer such that the aqueous botanical extract solution can be atomized into a room and easily contact numerous areas where dust mites are known to be present including, for example, bed linens, pillows, and carpets. In a preferred embodiment, the median drop size of the atomized aqueous botanical extract solution is less than 1000 micrometers to ensure sufficient contact with the dust mite feces.

Briefly, therefore, the present invention is directed to a method of neutralizing dust mite feces. The method comprises introducing a soluble botanical extract into water to form an aqueous botanical solution and contacting the dust mite feces with the aqueous botanical extract solution. The botanical extract has a BAPNA-Trypsin Inhibition ($IC^{50}\times 10^{-3}$ (%, v/v)) of from about 0.01 to about 500.

The invention is further directed to a method of neutralizing dust mite feces. The method comprises introducing a soluble botanical extract into water to form an aqueous botanical solution and contacting the dust mite feces with the aqueous botanical extract solution. The botanical extract has a BAPNA-Trypsin Inhibition ($IC_{50}\times10^{-3}$ (%, w/v)) of from about 0.01 to about 500.

The invention is further directed to a method of neutralizing dust mite feces. The method comprises introducing a water soluble botanical extract into water to form an aqueous botanical extract solution and contacting the dust mite feces with the aqueous botanical extract solution. The botanical extract has a BAPNA-Trypsin Inhibition ($IC^{50}\times 10^{-3}$ (%, v/v or w/v)) of from about 0.01 to about 500 and a solubility in water of at least about 0.5% by weight.

The invention is further directed to a method of neutralizing dust mite feces. The method comprises introducing a water soluble botanical extract into water to form an aqueous botanical extract solution and contacting the dust mite feces with the aqueous botanical extract solution. The botanical extract has a BAPNA-Trypsin Inhibition ($IC^{50}\times 10^{-3}$ (%, v/v or w/v)) of from about 0.01 to about 500 and a solubility in water of at least about 1% (v/v or w/v).

The invention is further directed to an aqueous composition for neutralizing dust mite feces. The composition comprises a water soluble botanical extract having a BAPNA-Trypsin Inhibition ($IC_{50}\times10^{-3}$ (%, v/v or w/v)) of from about 0.01 to about 500.

The invention is further directed to a method of neutralizing dust mite feces. The method comprises introducing a protease inhibitory, water soluble agent into water to form a protease inhibitory solution and contacting the dust mite feces with the protease inhibitory solution.

Other objects and features of this invention will be in part apparent and in part pointed out hereinafter.

DETAILED DESCRIPTION OF THE PREFERRED EMBODIMENTS

In accordance with the present invention, it has been discovered that certain botanical extracts, whether in powder form or in liquid form, can be effectively utilized to reduce the allergenicity of allergens including dust mite feces. Surprisingly, substantially water soluble botanical extracts having a BAPNA-Trypsin Inhibition ($IC_{50}\times10^{-3}$ (%, v/v or w/v)) of from about 0.01 to about 500 as described herein can be introduced into water to form an aqueous botanical extract solution which can be utilized in atomized form to treat large areas quickly and easily to neutralize dust mite feces allergens. In preferred embodiments, the botanical extracts used to form the botanical extract solution have a solubility in water of at least about 0.5% by weight, and more preferably at least about 1% by weight to ensure sufficient solubility of the botanical extract into the aqueous solution. Further, it is preferred that the median drop size of the atomized aqueous botanical extract solution be less than about 1000 micrometers to ensure effective coverage.

Dust mites and feces from dust mites are present throughout many areas of homes as discussed above. Dust mite feces has been repeatedly shown to contain high levels of serine proteases, which are known to cause allergic responses in some humans when inhaled into the nose, throat, and lungs. Through vigorous investigation and experimentation, the inventors discovered that numerous botanical extracts have strong protease inhibitory activity and have high solubility in water. This combination of protease inhibitory activity and solubility in water allows a concentrated aqueous botanical extract solution to be prepared in accordance with the present invention that can be contacted with the feces of dust mites resulting in the neutralization of the feces such that the dust mite feces become substantially non-allergenic. One important aspect of the present invention is that the botanical extracts act to neutralize the allergenic feces of the dust mite, and do not simply kill some dust mites while leaving the feces to continue to act as an allergen if inhaled. Because completely killing every dust mite in an area, such as a bedroom, and keeping the dust mites from returning is extremely difficult, if not impossible, the present invention is substantially advantageous in that the specific allergens themselves, the feces, are neutralized through contact with the atomized botanical extract. As discussed below, in some embodiments of the present invention, the botanical extract solution described herein can be utilized in combination with an additional agent capable of killing the dust mites. This combination provides a highly effective anti-allergenic system.

Numerous water soluble botanical extracts which provide the desired level of protease inhibitory activity can be used in the aqueous solutions of the present invention to neutralize dust mite feces. The botanical extracts useful in the practice of the present invention may be in solid form or in aqueous form. Regardless of whether the botanical extract is in solid form or aqueous form, as used herein, the term "water soluble" means soluble in water at a level of at least about 0.5% by weight, and preferably at least about 1% by weight. Typically, aqueous botanical extracts will have a much higher solubility in water. It will be recognized by one skilled in the art that many of the liquid botanical extracts described herein may be provided as mixtures of water, butylene glycol, glycerin, and the extracted botanical, or similar formulations. The extract formulation is soluble in water in part due to the use of butylene glycol as the solvent. As such, the botanical extracts themselves suitable for use in the present invention may be water soluble or hydrophilic solvent soluble. Common hydrophilic solvents include propylene glycol, butylene glycol, ethylene glycol, hexylene glycol, pentylene glycol, methyl propanediol, dipropylene glycol, and the like. Additionally, solvents such as ethanol or isopropyl alcohol may be utilized as solvents.

As used herein, the term "neutralize dust mite feces" means that the dust mite feces is rendered less allergenistic; that is, the dust mite feces, or components thereof, are a less potent allergen and are less likely to result in an allergic reaction in a human. Many botanical extracts are commercially available and typically are in one of three forms: (1) powderous solid; (2) aqueous solution comprising the botanical; or (3) oil. In solid form, the botanical extract is typically about 100% pure botanical extract, but may include a small percentage of other solids resulting from the purification procedures used to collect the botanical extract from the botanical source. When the botanical extract is available only as an aqueous solution or oil, the exact amount of botanical extract contained in the liquid may not be precisely known. Regardless, liquid botanical extracts can be tested and evaluated for use in the present invention as described herein without knowing the precise amount of botanical present in the solution.

In accordance with the present invention, the botanical extracts suitable for use in the aqueous solutions are substantially soluble in water. Preferably, the botanical extract is soluble in water at a level of at least about 0.5% by weight, and more preferably at least about 1% by weight. This solubility ensures that the botanical extract will be sufficiently soluble for introduction into the aqueous solutions as described herein such that the solution can be easily atomized. As one skilled in the art will recognize, higher solubilities are preferred.

Suitable botanical extracts for use with the methods and compositions of the present invention include those botanical extracts having serine protease inhibitory properties; that is, botanical extracts that inhibit the activity of the enzyme serine protease and reduce its ability to perform its intended cleaving function on a given substrate. Specifically, botanical extracts suitable for use include those botanical extracts having a BAPNA-Trypsin Inhibition ($IC_{50} \times 10^{-3}$ (%, v/v or w/v) of from about 0.01 to about 500, more preferably from about 0.01 to about 200, still more preferably from about 0.01 to about 100, more preferably from about 0.01 to about 20, and most preferably from about 0.01 to about 10. Whether the percentage is reported in volume/volume (v/v) or weight/volume (w/v) depends on whether the botanical extract is a powder or a liquid. One skilled in the art will recognize that the $IC_{50}$ values set forth herein can easily be converted to concentration percentages (representing the concentration of a given botanical required to reduce the activity of the target by 50%) by simply multiplying the value by $10^{-3}$; for example, an $IC_{50}$ value as reported herein of 500 would be equal to a concentration of botanical extract of 0.5%; that is, a concentration of 0.5% of the botanical would be required to reduce the activity of the target enzyme by 50%.

The BAPNA-Trypsin Inhibition $IC_{50}$ values described herein are determined for botanical extracts according to the BAPNA-Trypsin Inhibition Testing procedure set forth herein, and well known to those skilled in the art.

BAPNA-Trypsin Inhibition Test for Determination of $IC_{50}$ Values of Botanical Extracts Botanical extracts, whether in solid (powder) or liquid form, are tested for their ability to inhibit a model serine protease (porcine pancreatic trypsin) in solution as follows:

Step 1: Botanical extract testing solutions are prepared as follows when the botanical extract is a liquid: a 10% (v/v) starting solution is prepared by introducing 100 microliters of liquid botanical extract into one milliliter of Phosphate Buffered Saline (PBS), pH=7.4. If the liquid botanical extract is not soluble at a concentration of 10% (v/v) in PBS, a starting solution of 9% (v/v) is prepared and utilized as the starting solution described herein. If the 9% (v/v) starting testing solution is not soluble in PBS, starting testing solutions of 8% (v/v), 7% (v/v), etc. are prepared until the desired solubility is obtained. Serial dilutions of the starting solution for analysis are prepared using PBS at a pH of 7.4 as the diluent. For example, 7 serial dilutions of the 10% (v/v) starting solution can be made to prepare 8 different concentrations of botanical extract for testing: (1) 10%; (2) 5%; (3) 2.5%; (4) 1.25%; (5) 0.63%; (6) 0.31%; (7) 0.16%; and (8) 0.078%. Similar serial dilutions are made to prepare numerous samples if the starting testing solution concentration is less than 10%.

Botanical extract testing solutions are prepared as follows when the botanical extract is a solid: a 0.1% (w/v) starting solution is prepared by introducing 1 milligram of solid botanical extract into one milliliter of PBS, pH of 7.4. Serial dilutions of the starting solution are prepared using PBS, pH of 7.4, as the diluent. For example, 7 serial dilutions of the 0.1% (w/v) testing solution can be made to prepare 8 different concentrations of botanical extract for testing as described above.

Step 2: To the empty wells of a clear well plate, such as a NUNC IMMUNO clear 96 well plate (VWR Scientific Products, Chicago, Ill.), are added 150 microliters of 100 mM Tris buffer which has been adjusted to a pH of about 8.0 utilizing HCL. The Tris buffer is commonly known to those skilled in the art and can be prepared using Tris powder or Tris liquid.

Step 3: To the wells of the well plate to be utilized for testing the botanical extract (i.e., not the control wells to which 25 microliters of PBS is added in place of the botanical extract) is added 25 microliters of the botanical extract solution prepared under Step 1. For example, wells 1, 2, and 3 may have 25 microliters of the 10% (v/v) botanical extract solution added to them to analyze the 10% botanical extract solution in triplicate. Wells 4, 5, and 6 may then have 25 microliters of the 5% (v/v) botanical extract solution added to them to analyze the 5% botanical extract solution in triplicate, etc.

Step 4: A stock solution of the porcine pancreatic trypsin is then prepared by adding the protease (15,200 units/milligram, Sigma Chemical Company, St. Louis, Mo.) into 100 millimolar Tris buffer, pH adjusted to 8.0 with HCl to yield a concentration of 4 micrograms of trypsin/milliliter. To each well is then added 25 microliters of the protease.

Step 5: The well plates are then incubated at room temperature for 15 minutes.

Step 6: After incubation, 50 microliters of a 5 millimolar solution of N-benzyl-arginine-p-nitroaniline (BAPNA, Sigma Chemical Company, St. Louis, Mo.) is added to each of the wells. The BAPNA substrate is prepared as a stock solution by preparing a 50 millimolar solution of BAPNA in dimethylsulfoxide and diluting the solution to a 5 millimolar working solution with deionized water. One skilled in the art will recognize that the final concentration of botanical extract in the sample being tested is 1/10 of the concentration of the botanical extract solution as prepared under Step 1. For example, the 10% botanical extract solution prepared in step 1 becomes a 1% concentration of botanical extract in the well.

Step 7: After the BAPNA is added, the plate is inserted into a SPECTRAmax PLUS Microplate Reader (Molecular Devices, Sunnyvale Calif.), or similar instrument, and optical density measurements (405 nanometers) are taken every 20 seconds for a period of 5 minutes to monitor the color change of the solution. When trypsin cleaves the BAPNA substrate releasing the product p-nitroaniline, a color change occurs. The amount of color change occurring at 405 nanometers per minute corresponds to the amount of product produced per minute.

Reaction rates (optical density at 405 nanometers per minute) are determined with each concentration of botanical extract tested and the PBS control (no botanical extract). If the control wells were prepared in duplicate or triplicate, for example, the reaction rates from each of the wells were averaged. The data are used to determine an $IC_{50}$ value for each botanical extract plotting trypsin activity (y-axis) versus botanical extract concentration (percent w/v or v/v) (x-axis). $IC_{50}$ is defined as the concentration of the botanical extract that inhibits 50% of the trypsin activity.

In accordance with the present invention, the following botanical extracts have been found to have the desired protease inhibitory properties and are suitable for use in an aqueous solution for neutralizing dust mite feces as described herein: Apple Green Tea, Arkin Special, Arnica Special, Avocado, Avocado GW, Black Currant Green Tea, Cabbage Rose, Cat's Claw, Cemila Oleifera, Centella, Cranberry Green Tea, Dandelion, Garcinia, Grape Seed, Grapefruit Green Tea, Green Tea, Green Tea Concentrate, Green Tea HS, Hexaplant Richter, Hibiscus Special, Hydrocotyle GR, Lavender, Horse Chestnut, Milk Thistle, Orange Green Tea, Phytexcell Arnica, Purple Coneflower, Sage GW, Sage Special, Sedaplant Richter, St. John's Wort, Witchhazel GW, Yarrow, Green Tea Extra, Grape Seed Extract and White Tea 50%. Preferred botanical extracts include Green Tea Extra, Grape Seed Extract, and White Tea 50%.

The soluble botanical extracts having sufficient protease inhibitory activity described herein are introduced into water to form an aqueous botanical extract solution which is subsequently contacted with the dust mite feces to allow the botanical extract to interact with and reduce the allergenicity of the dust mite feces. The water source is not critical, and can be deionized water, distilled water, tap water, and the like. Although not required, it is preferred that the aqueous botanical extract solutions as described herein be adequately preserved to substantially prevent microbial contamination and thus improve the overall quality of the solution. One skilled in the art will recognize that there are a number of water soluble preservatives commercially available which would be suitable for use with the aqueous botanical extract solutions described herein.

The aqueous botanical extract solution can easily be atomized into an area to be treated, such as a bedroom or other room. As used herein, the term "atomized" means that the aqueous botanical extract solution is reduced to a spray form from liquid form, or volatilized. Atomization of the aqueous botanical extract solutions of the present invention can be accomplished utilizing various means including, for example, atomizers, aerosol sprayers, mechanical sprayers, misters, humidifiers, foggers, fumigating apparatuses, and the like. Both cold mist formulations and warm mist formulations including the aqueous botanical extract solutions are within the scope of the present invention. The aqueous botanical solution can also contain a small amount of dyes to color the product and/or a fragrance-to impart a pleasing odor to the solution. Both of these additives potentially enhance consumer appeal of the product.

The precise method of volatilizing the aqueous botanical extract solutions of the present invention to allow the botanical extract to contact the dust mite feces is not critical so long as the method employed can volatilize the aqueous solution sufficiently. Because house dust mites are typically very small in size, having a length of only about 250 microns to about 300 microns, it is preferable, although not critical, that the size of the droplets produced by the atomizing means be of such a size that they will sufficiently contact a majority of the dust mites and feces present in an area. As such, it is preferred that at least some of the atomized droplets of aqueous botanical extract solution have a medium drop size of no more than 1000 micrometers, more preferably no more than 500 micrometers, more preferably no more than about 200 micrometers, and most preferably no more than about 100 micrometers or less. These median drop sizes will allow a significant amount of the botanical extract to contact the dust mite feces present. Alternatively, a pesticidal composition could be introduced into the aqueous botanical extract solution and atomized simultaneously.

In another embodiment of the present invention, the aqueous botanical extract solutions described herein can be used in combination with a pesticidal, acaricidal, or other suitable agent which kills the dust mites upon application or treatment. This combination of applications would serve to not only neutralize the dust mite feces present, but also reduce the number of living dust mites. For example, a pesticidal composition capable of killing dust mites upon contact could first be sprayed or otherwise applied to an area such as a bedroom, to kill dust mites. After the pesticidal application, the aqueous botanical extracts of the present invention could be atomized as described herein into the area to neutralize the feces of the dust mites. Although the aqueous botanical extract solutions described herein are highly effective in neutralizing the dust mite feces when used alone, when used in combination with an agent that kills dust mites, the combination is also highly effective in controlling the amount of dust mite allergens present.

The present invention is illustrated by the following example which is merely for the purpose of illustration and is not to be regarded as limiting the scope of the invention or manner in which it may be practiced.

EXAMPLE 1

In this example, numerous botanical extracts, both in solid (powder) form and in aqueous liquid form, were analyzed for serine protease inhibitory activity using the BAPNA-Trypsin Inhibition Test described herein. Although referred to throughout the Example as "v/v," it should be realized that the concentration of the botanical extract would be referred to a "w/v" if the botanical extract was a solid. All of the botanical extracts tested were either in solid or aqueous form, and all liquids were soluble at a level of 10% by weight and all solids were essentially soluble at a level of 1% by weight.

The botanical extracts, the name of the company where the botanical extract was purchased, the location of the company, the lot number (if available), the catalog number (if available) and the $IC_{50}$ results for the botanical extracts tested in this Example are set forth in Table 1. Each liquid botanical extract listed in Table 1 was prepared for analysis as follows: A 10% (v/v) botanical extract solution in PBS (pH=7.4, Life Technologies, Rockville, Md.) was prepared by introducing 100 microliters of botanical extract into one milliliter of PBS. Serial dilutions of the 10% botanical solution in PBS were then made to prepare the following concentrations in addition to the 10% concentration; 5%, 2.5%, 1.25%, 0.63%, 0.31%, 0.16%, and 0.078%.

Each solid botanical extract listed in Table 1 was prepared for analysis as follows: A 0.1% (w/v) botanical extract solution in PBS (pH=7.4) was prepared by introducing 1 milligram of botanical extract into one milliliter of PBS. Serial dilutions were prepared from this solution for a total of eight testing solutions.

To the empty wells of a NUNC IMMUNO clear 96 well plate (VWR Scientific Products, Chicago, Ill.) was added 150 microliters of a 100 millimolar Tris buffer (Sigma Chemical Company, St. Louis, Mo.) with the pH adjusted to 8.0 utilizing HCl. Next, to allow for testing in triplicate, each concentration of botanical solution was added to three separate wells containing the Tris buffer. For control purposes, three wells had 25 microliters of the PBS solution introduced therein in place of any botanical extract solution.

A stock solution of porcine pancreatic trypsin (15,200 units/milligram, Sigma Chemical Company, St. Louis, Mo.) was then prepared by adding the porcine pancreatic trypsin into 100 millimolar Tris buffer, pH adjusted to 8.0 with HCL to yield a concentration of 4 micrograms/milliliter. To each well of the plate was then added 25 microliters of the 4 micrograms/milliliter trypsin.

After the porcine pancreatic trypsin was added to the wells of the plate, the well plates were incubated at room temperature for 15 minutes.

After incubation, 50 microliters of a 5 millimolar solution of N-benzyl-arginine-p-nitroaniline (BAPNA) was added to each of the wells on the plate. The BAPNA substrate was prepared as a stock solution by preparing a 50 millimolar solution of BAPNA in dimethylsulfoxide and diluting the solution to a 5 millimolar working solution with deionized water. This resulted in a total concentration of botanical extracts being tested from a working stock of 10% (v/v) botanical solution of (1) 1%; (2) 0.5%; (3) 0.25%; (4) 0.125%; (5) 0.063%; (6) 0.031%; (7) 0.016%; and (8) 0.0078%.

Immediately after the BAPNA was added, the plate was inserted into a SPECTRAmax PLUS 384 Microplate Reader (Molecular Devices, Sunnyvale, Calif.), and the optical density of each well was measured at 405 nanometers every 20 seconds for 5 minutes.

After the optical density data was collected, an $IC_{50}$ value was determined as set forth above for each botanical extract. The results are set forth in Table 1.

TABLE 1

| Botanical | Company | Location | Lot Number/ Catalog Number | $IC_{50}$ ($\times 10^{-3}$ (% v/v or w/v)) |
|---|---|---|---|---|
| Aloe Gel | Tri-K Industries | Northvale, N.J. | 970217/NA | 1000 (no effect) |
| Apple Extract | Gattefosse | Cedex, France | 23152 | 1000 (no effect) |
| Apple Green Tea | Dragoco | Totowa, N.J. | 2/037050/ L742477 | 11.5 |
| Arkin Special | Dragoco | Totowa, N.J. | 2/032581/ L647147 | 44.5 |
| Arnica Special | Dragoco | Totowa, N.J. | 2/034591/ L641060 | 39 |
| Avocado | Dragoco | Totowa, N.J. | 2/034599/ L645246 | 495 |
| Avocado GW | Dragoco | Totowa, N.J. | 2/031170/ L603922 | 19 |
| Black Currant B | Dragoco | Totowa, N.J. | 2/036100/ P331166 | 1000 (no effect) |
| Black Currant Green Tea | Dragoco | Totowa, N.J. | 2/037100/ P331166 | 12.5 |
| Cornflower | Gattefosse | Cedex, France | 23593/5009 | 1000 (no effect) |
| Cabbage Rose Extract. | Gattefosse | Cedex, France | 22223 | 14.5 |
| Calendula MCF 774 Hydro | Gattefosse | Cedex, France | 24243/5015 | 1000 (no effect) |
| Cat's Claw | Bio-botanica | Hauppauge, N.Y. | 951341/ 9945A | 16.5 |
| Cemila Oleifera Extract | Gattefosse | Cedex, France | 22423 | 4.5 |
| Centella | Bio-botanica | Hauppauge, N.Y. | 981177/ 9869A | 176 |
| Chamomile | Bio-botanica | Happauge, N.Y. | 980572/9831 | 1000 (no effect) |
| Chamomile Special | Dragoco | Totowa, N.J. | 2/033021/ 694633 | 1000 (no effect) |
| Chlorella | Bio-botanica | Hauppauge, N.Y. | 951289/9835 | 1000 (no effect) |
| Concombre GR 316 | Gattefosse | Cedex, France | 19190 | 1000 (no effect) |
| Cranberry B | Dragoco | Totowa, N.J. | 2/036600/ P15193 | 1000 (no effect) |
| Cranberry Green Tea | Dragoco | Totowa, N.J. | 2/037600/ 4100723 | 6.5 |
| Dandelion | Active organics- Glenn Corp | Lewisville, Tx. | S72041A/ 316310-11 | 88.5 |
| Dong Quai | Active organics- Glenn Corp | Lewisville, Tx. | S64418B/ 316320-11 | 1000 (no effect) |
| Drago-Oat- Active | Dragoco | Totowa, N.J. | 2/060900/ 25493 | 1000 (no effect) |
| Garcinia | Bio-botanica | Happauge, N.Y. | 951283/ 9861 | 400 |
| Ginseng GR 471 Hydro | Gattefosse | Cedex, France | 23268/5030 | 1000 (no effect) |
| Glenn of Oak | Glenn Corp. | St. Paul, Mn. | | 715 |
| Glenn of Orange | Glenn Corp. | St. Paul, Mn. | | 1000 (no effect) |
| Gotu Kola PG 5:1 | Bio-botanica | Hauppauge, N.Y. | | 1000 (no effect) |
| Grape Extract | Gattefosse | Cedex, France | 22151 | 1000 (no effect) |
| Grape Seed | Active organics- Glenn Corp | Lewisville, Tx. | S76920B/ 318560-11 | 39 |
| Grape Seed Extract | Dragoco | Totowa, N.J. | 2/03199/ P17400 | 0.048 |
| Grapefruit | Gattefosse | Cedex, France | 23439 | 1000 (no effect) |
| Grapefruit Green Tea | Dragoco | Totowa, N.J. | 2/037150/ L4100211 | 12.5 |
| Green Tea | Bio-botanica | Happauge, N.Y. | /9945 | 6 |
| Green Tea Conc. | Active organics- Glenn Corp | Lewisville, Tx. | 308463/ 300230-94 | 140 |

TABLE 1-continued

| Botanical | Company | Location | Lot Number/ Catalog Number | $IC_{50}$ ($\times 10^{-3}$ (% v/v or w/v)) |
|---|---|---|---|---|
| Green Tea Extra | Dragoco | Totowa, N.J. | 2/031598/ 3066 | 0.15 |
| Green Tea HS | Alban Muller Intl | Northvale, N.J. | 7114309/ | 15.6 |
| Hexaplant Richter | Chemisches Lab. | Berlin, Germany | 732431/243 | 29.5 |
| Hibiscus Special | Dragoco | Totowa, N.J. | 2/033115/ L651028 | 91.5 |
| Hydrocotyl GR | Gattefosse | Cedex, France | 22842/5038 | 59 |
| Hydrolite-5 | Dragoco | Totowa, N.J. | 2/016020/ 27033 | 1000 (no effect) |
| Kiwi | Gattefosse | Cedex, France | 23311 | 1000 (no effect) |
| White Nettle | Gattefosse | Cedex, France | 22571/5040 | 1000 (no effect) |
| Lavender | Gattefosse | Cedex, France | 21189 | 20 |
| Lemon Extract | Gattefosse | Cedex, France | 24126 | 1000 (no effect) |
| Lily | Gattefosse | Cedex, France | 23410/5044 | 1000 (no effect) |
| Horse Chestnut | Gattefosse | Cedex, France | 22043/5046 | 36 |
| Horse Chestnut | Indena-International Sourcing | Uppersaddle River, N.J. | EG042 | 12.5 |
| German Chamomile | Indena-International Sourcing | Uppersaddle River, N.J. | EG004 | 1000 (no effect) |
| Matricaria Extract | Gattefosse | Cedex, France | 21747 | 1000 (no effect) |
| Sweet Clover | Gattefosse | Cedex, France | 23316/5051 | 1000 (no effect) |
| Milk Thistle | Active organics-Glenn Corp | Lewisville, Tx. | S76894A/ 344000-11 | 215 |
| Nab Willow Bark Extract | Brooks Industries | S. Plainfield, N.J. | 28392 | 1000 (no effect) |
| Orange Green Tea | Dragoco | Totowa, N.J. | 2/037400/ P327911 | 9.5 |
| Phytexcell Arnica | Croda | Parsippany, N.J. | 972/34656 | 245 |
| Phytexcell Mulberry | Croda | Parsippany, N.J. | 1004/34684 | 1000 (no effect) |
| Phytoplenolin | Bio-botanica | Happauge, N.Y. | 980510/9870 | 760 |
| Purple Coneflower | Bio-botanica | Happauge, N.Y. | 951338/9852 | 21 |
| Raspberry | Gattefosse | Cedex, France | 23204 | 1000 (no effect) |
| Sage CL | Dragoco | Totowa, N.J. | 2/033294/ L640225 | 1000 (no effect) |
| Sage GW | Dragoco | Totowa, N.J. | 2/031770/ L619604 | 20 |
| Sage Special | Dragoco | Totowa, N.J. | 2/033291/ P312506 | 22 |
| Sedaplant Richter | Chemisches Lab. | Berlin, Germany | 732384/460 | 20 |
| St. John's Wort W/S | Dragoco | Totowa, N.J. | 2/032985/ L658926 | 27 |
| White Mistle Toe | Dragoco | Totowa, N.J. | 2/033141/ L653324 | 1000 (no effect) |
| White Tea 50% | Dragoco | Totowa, N.J. | 10521/ C-14235 | 0.098 |
| Witchhazel GW | Dragoco | Totowa, N.J. | 2/031340/ L651033 | 99 |
| Yarrow | Bio-botanica | Happauge, N.Y. | 951336/9958 | 80 |

As the data in Table 1 indicates, $IC_{50}$ values determined for the botanical extracts tested ranged from 0.048 to 1000 (no inhibition detected). This would indicate that the botanical extract with an $IC_{50}$ value of 0.048 (Grape Seed Extract) is highly effective in neutralizing dust mite feces whereas the botanical extract with a value of 1000 has little to no effect.

In view of the above, it will be seen that the several objects of the invention are achieved. As various changes could be made in the above-described methods and compositions for neutralizing dust mite feces without departing from the scope of the invention, it is intended that all matter contained in the above description be interpreted as illustrative and not in a limiting sense.

What is claimed is:

1. A method of neutralizing dust mite feces, the method comprising:
   introducing a grape seed extract into water to form an aqueous grape seed extract solution, the grape seed extract having a BAPNA-Trypsin Inhibition ($IC_{50} \times 10^{-3}$ (%, v/v)) of from about 0.01 to about 500; and
   contacting the dust mite feces with the aqueous grape seed extract solution.

2. The method as set forth in claim 1 wherein the BAPNA-Trypsin Inhibition of the grape seed extract is from about 0.01 to about 200.

3. The method as set forth in claim 1 wherein the BAPNA-Trypsin Inhibition of the grape seed extract is from about 0.01 to about 100.

4. The method as set forth in claim 1 wherein the BAPNA-Trypsin Inhibition of the grape seed extract is from about 0.01 to about 20.

5. The method as set forth in claim 1 wherein the BAPNA-Trypsin Inhibition of the grape seed extract is from about 0.01 to about 10.

6. The method as set forth in claim 1 wherein the contacting the dust mite feces with the aqueous grape seed extract solution comprises atomizing the aqueous grape seed extract solution and contacting the dust mite feces with the atomized aqueous grape seed extract solution.

7. The method as set forth in claim 6 wherein the atomized aqueous grape seed extract solution has a median drop size of no more than about 1000 micrometers.

8. The method as set forth in claim 6 wherein the atomized aqueous grape seed extract solution has a median drop size of no more than about 500 micrometers.

9. The method as set forth in claim 6 wherein the atomized aqueous grape seed extract solution has a median drop size of no more than about 200 micrometers.

10. The method as set forth in claim 6 wherein the atomized aqueous grape seed extract solution has a median drop size of no more than about 100 micrometers.

11. The method as set forth in claim 6 wherein the grape seed extract has a solubility in water of at least about 0.5% by weight.

12. The method as set forth in claim 6 wherein the grape seed extract has a solubility in water of at least about 1% by weight.

13. A method of neutralizing dust mite feces, the method comprising:
    introducing a grape seed extract into water to form an aqueous grape seed extract solution, the grape seed extract having a BAPNA-Trypsin Inhibition ($IC^{50} \times 10^{-3}$ (%, w/v)) of from about 0.01 to about 500; and
    contacting the dust mite feces with the aqueous grape seed extract solution.

14. The method as set forth in claim 13 wherein the BAPNA-Trypsin Inhibition of the grape seed extract is from about 0.01 to about 200.

15. The method as set forth in claim 13 wherein the BAPNA-Trypsin Inhibition of the grape seed extract is from about 0.01 to about 100.

16. The method as set forth in claim 13 wherein the BAPNA-Trypsin Inhibition of the grape seed extract is from about 0.01 to about 20.

17. The method as set forth in claim 13 wherein the BAPNA-Trypsin Inhibition of the grape seed extract is from about 0.01 to about 10.

18. The method as set forth in claim 13 wherein the contacting the dust mite feces with the aqueous grape seed extract solution comprises atomizing the aqueous grape seed extract solution and contacting the dust mite feces with the atomized aqueous grape seed extract solution.

19. The method as set forth in claim 18 wherein the atomized aqueous grape seed extract solution has a median drop size of no more than about 1000 micrometers.

20. The method as set forth in claim 18 wherein the atomized aqueous grape seed extract solution has a median drop size of no more than about 500 micrometers.

21. The method as set forth in claim 18 wherein the atomized aqueous grape seed extract solution has a median drop size of no more than about 200 micrometers.

22. The method as set forth in claim 18 wherein the atomized aqueous grape seed extract solution has a median drop size of no more than about 100 micrometers.

23. The method as set forth in claim 13 wherein the grape seed extract has a solubility in water of at least about 0.5% by weight.

24. The method as set forth in claim 13 wherein the grape seed extract has a solubility in water of at least about 1% by weight.

* * * * *